United States Patent [19]

White

[11] Patent Number: 5,288,486
[45] Date of Patent: Feb. 22, 1994

[54] ALCOHOL-BASED ANTIMICROBIAL COMPOSITIONS

[75] Inventor: John H. White, St. Louis, Mo.

[73] Assignee: Calgon Corporation, Pittsburgh, Pa.

[21] Appl. No.: 676,412

[22] Filed: Mar. 29, 1991

Related U.S. Application Data

[63] Continuation of Ser. No. 7,159, Jan. 26, 1987, abandoned, which is a continuation of Ser. No. 791,668, Oct. 28, 1985, abandoned.

[51] Int. Cl.$^5$ .............................................. A61K 31/74
[52] U.S. Cl. ........................... 424/78.08; 424/78.07; 514/848; 514/828
[58] Field of Search ............. 424/78, 80, 78.08, 78.07; 514/947, 848, 828

[56] References Cited

U.S. PATENT DOCUMENTS

| | | | |
|---|---|---|---|
| 4,199,564 | 4/1986 | Silver | 424/80 |
| 4,284,649 | 8/1981 | Wiczer | 514/944 |
| 4,310,509 | 1/1982 | Berglund et al. | 424/80 |
| 4,542,012 | 9/1983 | Dell | 424/80 |

FOREIGN PATENT DOCUMENTS 60-61518  4/1985  Japan .................................. 514/944

OTHER PUBLICATIONS

Klucel–Hercules, pp. 1–32, 1981.
Hercules Brochure VC–439E, pp. 4–35, 1981.

*Primary Examiner*—Peter F. Kulkosky
*Attorney, Agent, or Firm*—Richard S. Parr; Michael C. Sudol

[57] ABSTRACT

The instant invention is directed to a process for enhancing the efficacy of alcohol-based skin antiseptics comprising adding at least one alcohol-soluble viscosifying agent to an alcohol-based disinfectant, thereby lowering its alcohol evaporation rate and markedly increasing the exposure time that disinfecting concentrations of alcohol are present on skin. The improved alcohol-based antiseptics thus obtained are also claimed.

2 Claims, No Drawings

ALCOHOL-BASED ANTIMICROBIAL COMPOSITIONS

This is a continuation of application Ser. No. 007,159 filed Jan. 26, 1987, abandoned, which is a continuation of the parent case, Ser. No. 791,668 filed Oct. 28, 1985 abandoned.

BACKGROUND OF THE INVENTION

Alcohol-based skin disinfectants, because of their high vapor pressure, evaporate quickly. Thus, when they are applied to skin, alcohol concentration and contact time with bacteria and other microorganisms are minimized due to evaporative loss. The inventor has discovered a method of decreasing evaporation of alcohol skin disinfectants comprising adding alcohol-soluble viscosifying agents to these disinfectants, thereby increasing the exposure time and alcohol concentration of the disinfectant on the skin.

Alcohol solutions containing 30–90%, by weight, alcohol are often used by healthcare personnel to disinfect hands and for localized skin disinfection at the site of an invasive medical procedure. These alcohol compositions are very drying to the skin, evaporate quickly, and are easily spilled due to their watery nature. These shortcomings are overcome by the instantly claimed method and compositions.

DESCRIPTION OF THE INVENTION

The instant invention is directed to a method for enhancing the efficacy of alcohol-based skin disinfectants or antiseptics comprising adding about 0.1 to about 10 percent, based on total formulation weight, of at least one alcohol-soluble viscosifying agent to said alcohol-based disinfectant or antiseptic, thereby retarding evaportion of said alcohol-based disinfectant or antiseptic and increasing its contact time with the skin being treated and its antimicrobial effectiveness.

The instant invention is also directed to improved alcohol-based skin disinfectants or antiseptics which comprise 30–90%, based on total formulation weight, of an alcohol, 0.1 to 10%, by weight, based on total formulation weight, an alcohol-soluble viscosifying agent and the balance water.

The present invention employs a viscosifying agent to retard alcohol evaporation, thereby allowing more efficient use of alcohols as skin disinfectants or antiseptics.

The phrase "viscosifying agent", as used herein, refers to any chemical compound which tends to thicken an alcohol/water composition, thereby lessening the evaporation rate of the alcohol. Any alcohol-soluble viscosifying agent can be used. Preferred viscosifying agents are selected from the group consisting of hydroxypropyl cellulose polymers, polyvinyl pyrrlidones, and polymeric quaternary ammonium salts of hydroxyethyl cellulose reacted with a trimethyl ammonium substituted epoxide. While the molecular weight of the viscosifying agent is not critical, these preferred viscosifying agents are polymers with molecular weights sufficient to produce composition viscosities of at least 40 centipoise, when added to alcohol-based antimicrobial compositions at recommended dosages. More preferably, the viscosifiers produce viscosities of about 50 to about 500 cps in the final compositions.

The alcohol-soluble viscosifying agent should be added to an alcohol composition at a dosage of from about 0.1 to about 10%, based on total formulation weight. Preferably, the viscosifying agent should be added at a dosage of from about 0.1 to 5%, based on total formulation weight, and most preferably, the dosage should be 0.5 to 2.0%, based on total formulation weight.

Most preferred as viscosifying agents are hydroxypropyl cellulose polymers. For example, there may be mentioned Klucel HF and Klucel EF, which are hydroxypropyl cellulose ethers having molecular weights of about 1,000,000 and 60,000, respectively. These products are commercially available from Hercules, Incorporated. Hydroxypropyl cellulose polymers substantially reduce evaporation loss, thereby improving antibacterial efficacy.

Alcohol-based skin disinfectants and antiseptics are well-known in the art. As used herein, the terms "disinfectant" and "antiseptic" refer to those mixtures which are applied to skin for the purpose of killing bacteria and microorganisms on the skin. Such mixtures may be used as surgical scrub hand washes, patient pre-operative preparations, and as general healthcare hand washes. Other uses will become apparent to those skilled in the art and are intended to be within the scope of this invention.

While any water-soluble alcohol can, in theory, be used, the preferred alcohols for use in the alcohol-based compositions of this invention are selected from the group consisting of n-propyl alcohol, isopropyl alcohol and ethyl alcohol. From an antimicrobial standpoint, n-propyl alcohol is better than isopropyl alcohol, which in turn is better than ethyl alcohol.

The instant disinfectant compositions comprise: 30–90%, based on total formulation weight, an alcohol; 0.1–10%, based on total formulation weight, an alcohol-soluble viscosifying agent; and the balance water. Preferably, the alcohol concentration, based on total formulation weight, is 50–70%, and most preferably, 55–65%. Additionally, these compositions may contain fragrances, coloring agents, detackifiers such as cetyl lactate and additional antimicrobials without departing from the spirit of this invention.

As examples of preferred compositions, the following may be listed. These examples are not intended to limit the scope of the invention.

Formulation 1:
  30–75 g n-propyl alcohol;
  0.25–5.0 g hydroxypropyl cellulose;
  color and fragrance as desired;
  10–60 g deionized or distilled water.

Formulation 2:
  30–75 g isopropyl alcohol;
  0.25–5.0 g hydroxypropyl cellulose;
  color and fragrance as desired;
  10–60 ml deionized or distilled water.

Formulation 3:
  40–80 g 95% ethyl alcohol;
  0.25–5.0 g hydroxypropyl cellulose;
  color and fragrance as desired;
  5–50 ml deionized or distilledwater.

Formulation 4:
  30–75 g 2-isopropyl alcohol;
  0.25–5.0 g hydroxypropyl cellulose;
  0.5–2.0 g polymer of dimethyldiallyl ammonium chloride (Merquat 100, used as an emollient, available from Calgon Corporation, Pittsburgh, Pa.);
  0.1–0.2% para-chloro-meta-xylenol*;
  color and fragrance as desired;
  10–60 ml deionized or distilled water.

Formulation 5:
- 30–75 g isopropyl alcohol;
- 0.25–5.0 g hydroxypropyl cellulose;
- 0.5–2.0 g octyl palmitate (emollient);
- 0.25–0.5 g polymer of dimethyldiallyl ammonium chloride;
- 0.1–0.5% chlorhexidine gluconate*;
- color and fragrance as desired;
- 10–60 ml deionized or distilled water.

Formulation 6:
- 30–75 g isopropyl alcohol;
- 0.25–5.0 g hydroxypropyl cellulose;
- 0.5–2.0 g cetyl lactate;
- 0.25–0.5 g polymer of dimethyldiallyl ammonium chloride;
- color and fragrance as desired;
- 10–60 ml deionized or distilled water.

*para-chloro-meta-xylenol and chlorhexidine gluconate leave a residual antimicrobial agent on the skin after the alcohol has evaporated.

Examples 1-28

The following examples demonstrate the retardation of alcohol evaporation using viscosifying agents. Additionally, these examples demonstrate the antimicrobial efficacy of evaporation-stabilized, alcohol-based disinfectant/antiseptic compositions using pig skins as test substrates.

Preparation of Pig Skin:

Mature adult pig hides from freshly killed pigs were obtained from a slaughterhouse. The hides were washed using cold water and dehaired using a large animal clipper. After dehairing, the hides were cut into smaller sections with a scalpel, rinsed in cold water, placed in plastic bags, sealed and frozen.

Prior to use, each pigskin was tested for the presence of residual antibiotics. The method used was to randomly cut plugs, using a #7 cork borer, from the hide being tested and place them skin side down onto individual agar plates seeded with the test organisms. If a zone of inhibition surrounding the plug developed, the skin contained residual antibiotics and was not used.

Before use in a test, a section of pig skin was thawed, destubbled using a disposable razor, and defatted using a scalpel. The skin section was then rinsed in cold tap water and cut into 3 cm×3 cm pieces using a scalpel. The 3 cm×3 cm pieces were glued onto individual mounting holders (plastic caps approximately 4 to 5 cm in diameter or other suitable holders) with epoxy adhesive such that the skin surface was exposed. Two pieces of mounted skin were used for each sample tested. The mounted skins were placed into 100×20 mm petri dishes which contained a 7.0 cm filter paper disc moistened with approximately 1 ml of water to prevent drying. The prepared skins were placed in a refrigerator overnight.

Test Conditions:

The specific conditions used for the pig skin tests were as follows:
- less than or equal to $10^7$ organisms per cc mixed inoculum consisting of Serratia marcescens (ATCC 990), Escherichia coli (ATCC 8739), Staphylococcus aureus (ATCC 6538), Pseudomonas aeruginosa (ATCC 9027) and Canaida albicans (ATCC 10231);
- less than or equal to 2 hour incubation time between inoculation and treatment;
- 0.1 ml test sample;
- 15 second treatment (rubbing); and
- 3 minute air dry before imprinting.

Application of Test Organisms:

Suspensions of the various organisms were made by overlaying an overnight agar slant culture with 10 mls of Butterfield Buffer and gently rubbing the agar surface with a sterile pipet. These suspensions were mixed together to give a mixed inoculum of approximately $10^9$ microorganisms per ml. This mixed inoculum was further diluted to give either $10^7$ or $10^5$ organisms per ml depending upon the test conditions desired. One of two pieces of skin was inoculated with 0.1 ml of the diluted inoculum. The two pieces of skin were then rubbed together for 15 seconds and incubated at 30° C. for either 15 minutes or up to 2 hours depending on test conditions desired.

Application of Alcoholic Preparations:

Three alcohols, n-propyl alcohol, isopropyl alcohol and ethyl alcohol, were tested. One of two pieces of inoculated skin was treated with 0.1 ml of the desired alcohol preparation. The two pieces of skin were then rubbed together for 15 seconds and allowed to air dry for 3 minutes to simulate normal evaporation before imprinting the skin samples onto the surface of a neutralizing growth media (Standard Methods Agar with Lecithin and Polysorbate 80 from BBL).

Imprints were made by inverting the mounting holder anct pressing the treated skin onto the agar surface. Imprints were made after 3, 10 and 30 minutes and 1 hour. The plates were graded to indicate the extent of organism growth in the imprint. All of the samples were coded and graded blind to eliminate operator bias.

Ratings of 0 to 10 were given to denote coverage; i.e. 0=no visible growth, 1=10% of the imprint surface covered, 5=50% of the imprint surface covered, etc.

Evaporation Rate Determination:

A measured volume of test solution was added near the center of two thicknesses of 12.5 cm filter paper in a large 150 mm petri dish. The dish was placed on a top loading balance sensitive to 0.01 g which was shielded on three sides and top against drafts and, as extra precaution, the air conditioner was turned off during the test period.

Weight readings were made each 30 seconds over a six-minute period demonstrating uniformity of loss over this period. Values reported are the average loss/minute over six minutes in mg/min. Each value reported represents a separate observation series.

Results are shown in Table I, below.

TABLE I

Evaporation Rate-Pigskin Imprint Biological Comparison

| Example No. | Alcohol (% b/v) | Viscosifier 4 ml Sample (% w/w) | Average Evaporation Loss mg/min Run 1 | Run 2 | Coverage Rating** Imprint 2 min. | Imprint 10 min. | Imprint 30 min. | Imprint 1 hour |
|---|---|---|---|---|---|---|---|---|
| 1 | 40% IPA | 0% Klucel | 6.67 | 7.80 | | | | |
| 2 | 40% IPA | 0.25% Klucel | 4.17 | 4.17 | | | | |

TABLE I-continued

Evaporation Rate-Pigskin Imprint Biological Comparison

| Example No. | Alcohol (% b/v) | Viscosifier 4 ml Sample (% w/w) | Average Evaporation Loss mg/min Run 1 | Run 2 | Coverage Rating** Imprint 2 min. | Imprint 10 min. | Imprint 30 min. | Imprint 1 hour |
|---|---|---|---|---|---|---|---|---|
| 3 | 40% IPA | 0.5% Klucel | 2.67 | 3.00 | | | | |
| 4 | 60% IPA | 0% Klucel | 7.5* | 5.67* | 10 | 10 | 10 | 10 |
| 5 | 60% IPA | 0.25% Klucel | 3.50 | 3.00 | 10 | 9.5 | 10 | 9.5 |
| 6 | 60% IPA | 0.5% Klucel | 3.16 | 2.83 | 9.5 | 10 | 9.5 | 9 |
| 7 | 60% IPA | 1.0 Klucel | 2.0 | 1.67 | 3 | 4 | 4 | 4 |
| 8 | 60% IPA | 3.0% Klucel | — | — | 3 | 3 | 3 | 3 |
| 9 | 80% IPA | 0% Klucel | 8.33* 7.50 | 4.33* 7.17 | 1.5 | 2 | 2 | 2 |
| 10 | 80% IPA | 0.25% Klucel | 4.00 | 3.33 | | | | |
| 11 | 80% IPA | 0.5% Klucel | 3.00 | 4.16 | | | | |
| 12 | 80% IPA | 0.5% Klucel | — | — | 1 | 1.5 | 1.5 | 1 |
| 13 | 60% n-Propanol | 0.0% Klucel | — | — | — | 5 | 5 | 5 |
| 14 | 60% n-Propanol | 0.5% Klucel | — | — | — | 2 | 2 | 2 |
| 15 | 60% n-Propanol | 0.75% Klucel | — | — | — | | 2 | 2 |
| 16 | 60% IPA | 0.5% Klucel and 0.2% UCAR | — | — | — | 6.5 | 5.5 | 5.0 |
| 17 | 60% IPA | 0.5% Klucel and 0.5% UCAR | — | — | — | 3.0 | 3.5 | 3.5 |
| 18 | 60% IPA | 0.5% Klucel and 0.5% UCAR | — | — | — | 2.5 | 2.5 | 2.5 |
| 19 | 40% IPA | 0% Klucel | — | — | 10 | 10 | 10 | 10 |
| 20 | 40% IPA | 0.5% Klucel | — | — | 8 | 8.5 | 8.5 | 8 |
| 21 | 40% IPA | 1.0% Klucel | — | — | 9.5 | 9.5 | 9.5 | 9.5 |
| 22 | 40% IPA | 2.0% Klucel | — | — | 8 | 8 | 7.5 | 7.5 |
| 23 | 60% Ethanol | 0% Klucel | 5.67 | 8.17 | 7.5 | 7 | 6 | 5 |
| 24 | 60% Ethanol | 0.5% Klucel | 1.67 1.33 | 2.5 — | 6 | 6 | 5 | 4 |
| Use 2 ml Sample: | | | | | | | | |
| 25 | 60 % IPA | 0% Klucel | 4.83 | 6.67 | | | | |
| 26 | 60% IPA | 0.5% Klucel | 2.17 | 2.00 | | | | |
| Use 6 ml Sample: | | | | | | | | |
| 27 | 60% IPA | 0% Klucel | 8.83 | 8.67 | | | | |
| 28 | 60% IPA | 0.5% Klucel | 3.83 | 3.67 | | | | |

*Average of two tests.
**Coverage Rating: 0 = No growth 10 = 100% coverage 5 = 50% coverage.
Klucel = Klucel HF (hydroxypropyl cellulose), unless otherwise indicated as Klucel EF, available from Hercules, Inc.
UCAR = Ucare Polymer JR-400 (quaternary ammonium salt of hydroxyethyl cellulose reacted with trimethylammonium substituted epoxides), available from Union Carbide Corporation.
These examples demonstrate evaporation retardation and the improved antibacterial activity of the instant invention.

What is claimed is:

1. A method for enhancing the efficacy of an alcohol-based skin disinfectant containing about 30 to 90 percent, based on total composition weight, of at least one alcohol selected from the group consisting of n-propyl alcohol, isopropyl alcohol and ethyl alcohol comprising adding about 0.25 to about 5 percent, based on total composition weight, of at least one alcohol-soluble hydroxypropyl cellulose polymer viscosifying agent to said alcohol-based skin disinfectant, thereby increasing its antimicrobial effectiveness *against Serratia marcescens, Escherichia coli, Staphylococcus aureus, Pseudomonas aeruginosa or Candida albicans.*

2. The method of claim 1, wherein said alcohol-based skin disinfectant contains isopropyl alcohol, and wherein about 0.5 to about 2% of said alcohol-soluble hydroxypropyl cellulose polymer viscosifying agent is added.

* * * * *